US012747266B2

(12) United States Patent
Soung et al.

(10) Patent No.: US 12,747,266 B2
(45) **Date of Patent: *Sep. 29, 2026**

(54) ANTIMICROBIAL PEPTIDE WITH EXCELLENT MICROBIAL CYTOPLASM ELUTION EFFECT

(71) Applicant: CELLICON LAB INC., Daejeon (KR)

(72) Inventors: Min Gyu Soung, Daejeon (KR); Bo Kyung Park, Daejeon (KR); Won Suk Choi, Daejeon (KR); Young Pil Jeong, Daejeon (KR); Ji Hyun Park, Sejong-si (KR); Jae Hoo Park, Daejeon (KR)

(73) Assignee: CELLICON LAB INC., Daejeon (KR)

( * ) Notice: Subject to any disclaimer, the term of this patent is extended or adjusted under 35 U.S.C. 154(b) by 406 days.

This patent is subject to a terminal disclaimer.

(21) Appl. No.: 18/270,806

(22) PCT Filed: Nov. 5, 2021

(86) PCT No.: PCT/KR2021/016051

§ 371 (c)(1),
(2) Date: Jul. 3, 2023

(87) PCT Pub. No.: WO2022/163978

PCT Pub. Date: Aug. 4, 2022

(65) Prior Publication Data

US 2025/0270256 A1 Aug. 28, 2025

(30) Foreign Application Priority Data

Jan. 27, 2021 (KR) ........................ 10-2021-0011657

(51) Int. Cl.

| | |
|---|---|
| ***C07K 7/08*** | (2006.01) |
| ***A61K 8/64*** | (2006.01) |
| ***A61K 38/00*** | (2006.01) |
| ***A61P 31/04*** | (2006.01) |
| ***A61Q 17/00*** | (2006.01) |

(52) U.S. Cl.

CPC .................. *C07K 7/08* (2013.01); *A61K 8/64* (2013.01); *A61P 31/04* (2018.01); *A61Q 17/005* (2013.01); *A61K 38/00* (2013.01)

(58) Field of Classification Search

CPC .. C07K 7/08; A61K 8/64; A61K 38/00; A61P 31/04

See application file for complete search history.

(56) References Cited

U.S. PATENT DOCUMENTS

| | | | | |
|---|---|---|---|---|
| 2010/0016167 A1 | 1/2010 | Bardaji Rodriguez et al. | | |
| 2020/0318125 A1 | 10/2020 | Numata et al. | | |
| 2025/0011364 A1* | 1/2025 | Soung | .................... | A61K 38/10 |
| 2025/0073337 A1* | 3/2025 | Soung | .................... | A61K 9/127 |

FOREIGN PATENT DOCUMENTS

| | | | | |
|---|---|---|---|---|
| KR | 10-2016-0025950 A | 3/2016 | | |
| KR | 10-2016-0025953 A | 3/2016 | | |
| KR | 10-2017-0106571 A | 9/2017 | | |
| KR | 10-2019-0004677 A | 1/2019 | | |
| KR | 10-2019-0088683 A | 7/2019 | | |
| KR | 10-2020-0017912 A | 2/2020 | | |
| WO | WO-2021247965 A2 * | 12/2021 | ............. | A61K 38/08 |

OTHER PUBLICATIONS

Alves, C. S et al., "*Escherichia coli* Cell Surface Perturbation and Disruption Induced by Antimicrobial Peptides BP100 and pepR," *The Journal of Biological Chemistry*, 285.36 (2010): 27536-27544.
Office Action issued in Japanese Patent Application No. 2023-540908, dated Jul. 30, 2024.
Kaiser, E. et al., "Color Test for Detection of Free Terminal Amino Groups in the Solid-Phase Synthesis of Peptides," *Anal Biochem.*, 34 (1970): 595-598.
Extended European Search Report issued in European Patent Application No. 21923387.1, dated Nov. 18, 2024.
Torcato, I. M. et al., "Design and characterization of novel antimicrobial peptides, R-BP100 and RW-BP100, with activity against Gram-negative and Gram-positive bacteria," Biochimica et Biophysica Acta, 1828 (2013): 944-955.
Zhang, B. et al., "Synthesis and biological evaluation of novel peptides based on antimicrobial peptides as potential agents with antitumor and multidrug resistance-reversing activities," *Chem Biol Drug Des.*, 90 (2017): 972-980.

* cited by examiner

*Primary Examiner* — Melissa L Fisher
*Assistant Examiner* — Archana Varadaraj
(74) *Attorney, Agent, or Firm* — pH IP Law

(57) ABSTRACT

The present disclosure relates to an antimicrobial peptide, a derivative thereof, or a fragment thereof; a polynucleotide encoding the antimicrobial peptide, a derivative thereof, or a fragment thereof; and a carrier for external skin preparation, a cosmetic composition, a quasi-drug composition, and a pharmaceutical composition containing the antimicrobial peptide, a derivative thereof, or a fragment thereof.

8 Claims, 5 Drawing Sheets

Specification includes a Sequence Listing.

[FIG. 1A-B]
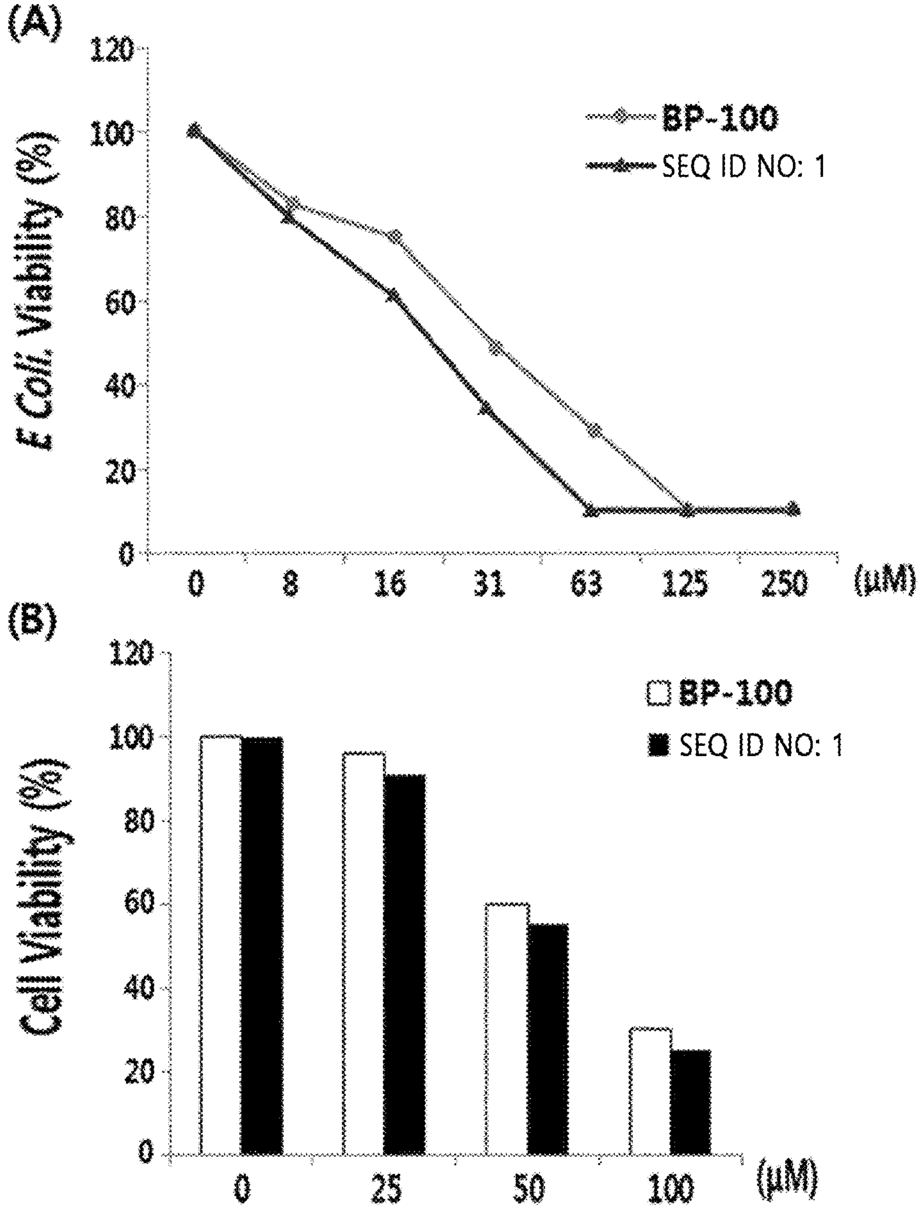

[FIG. 2A-B]
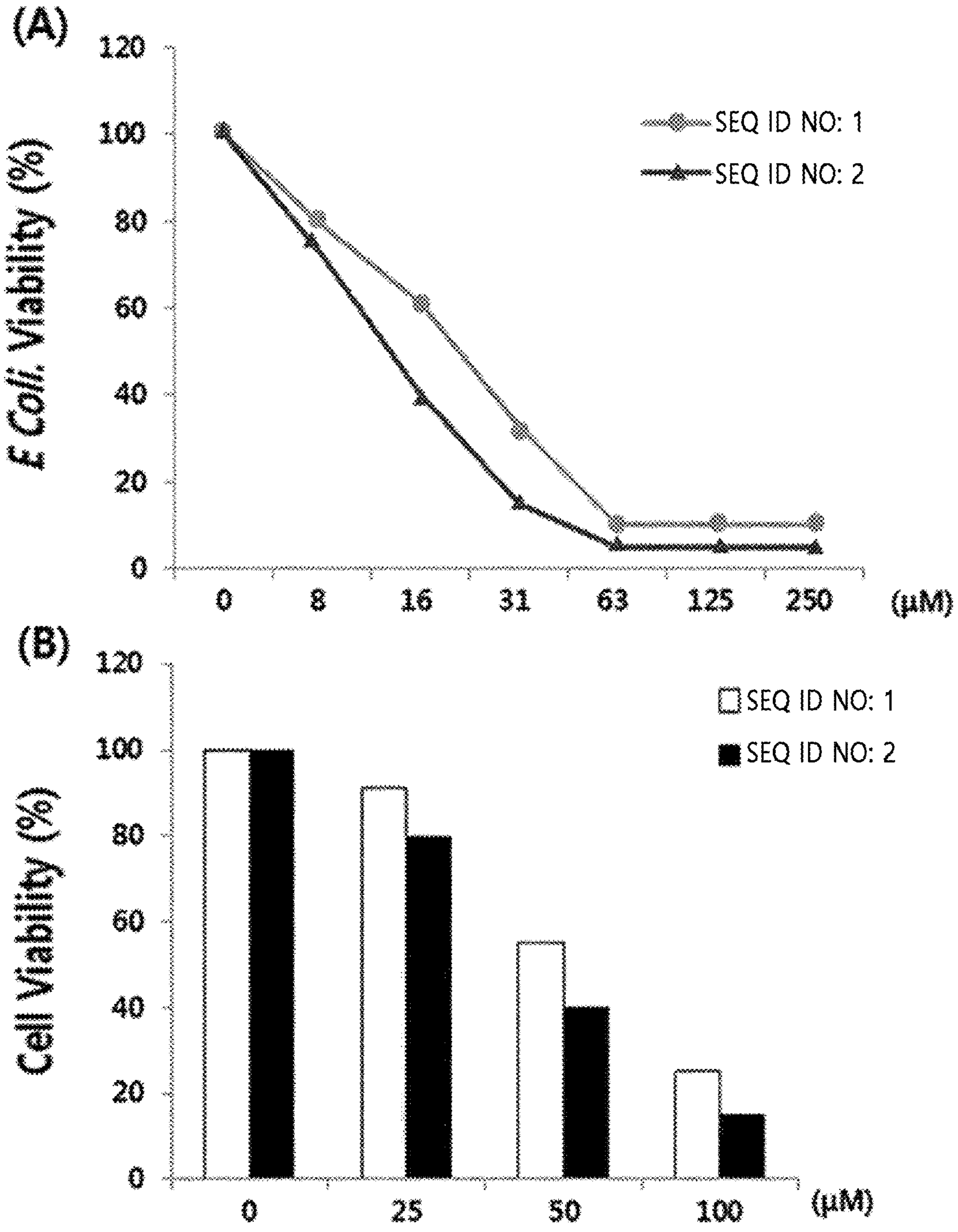

[FIG. 3A-B]
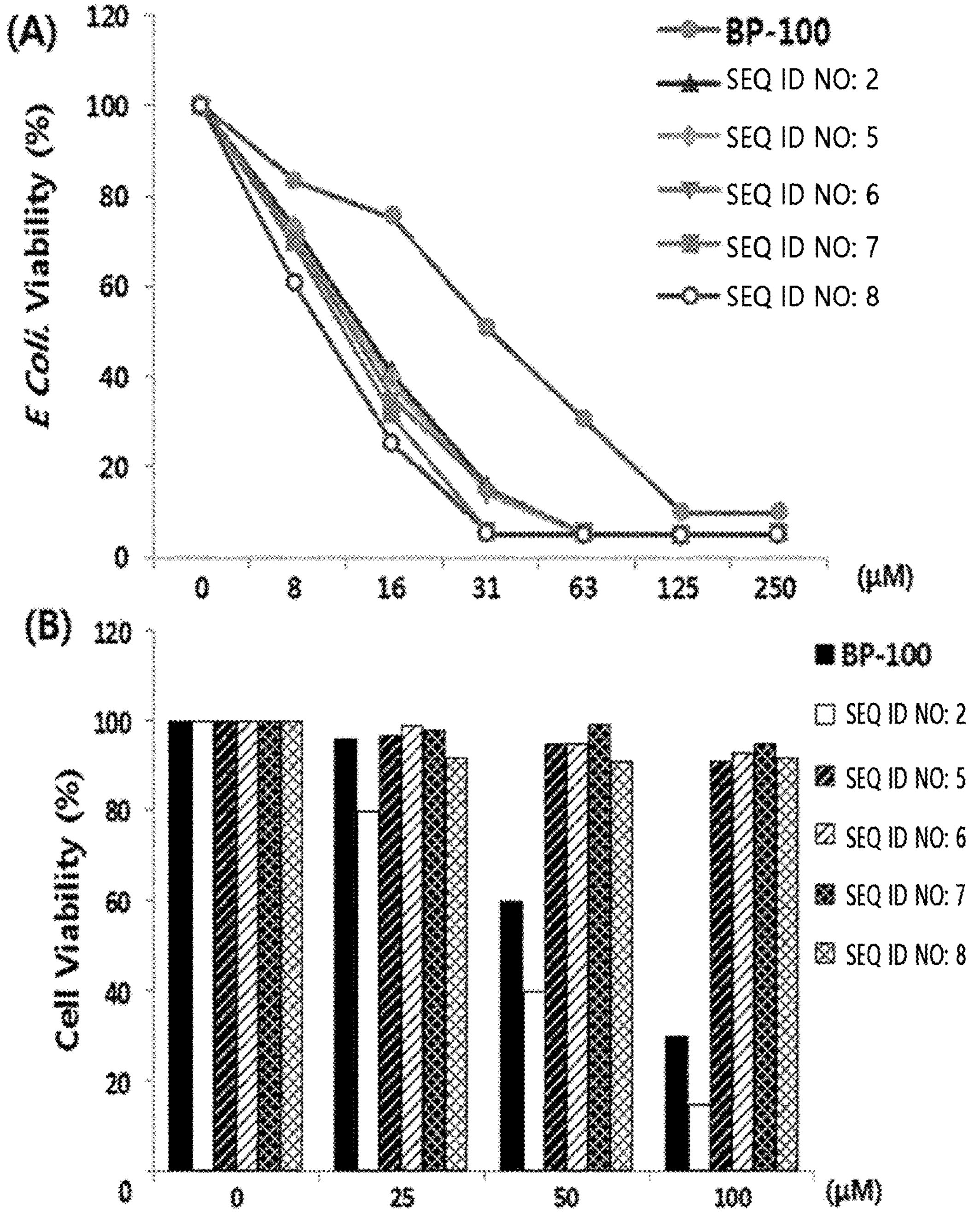

[FIG. 4A-B]
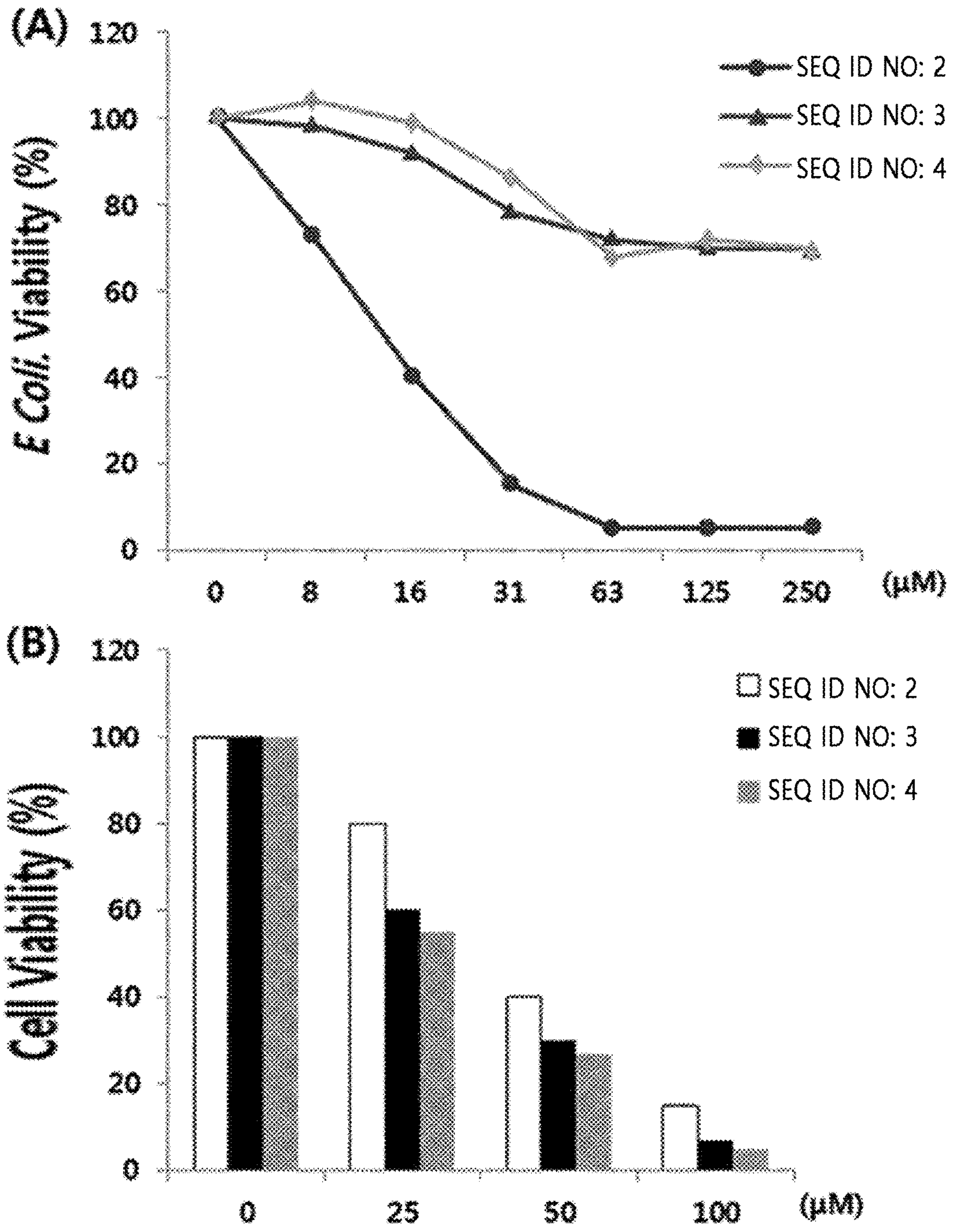

[FIG. 5]
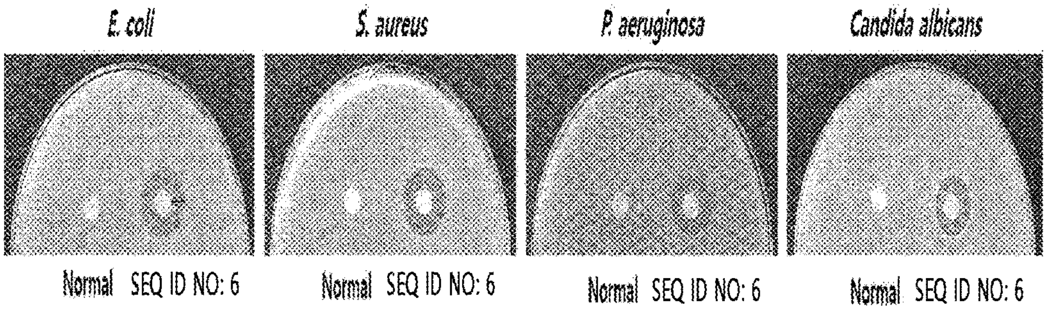
[FIG. 6]
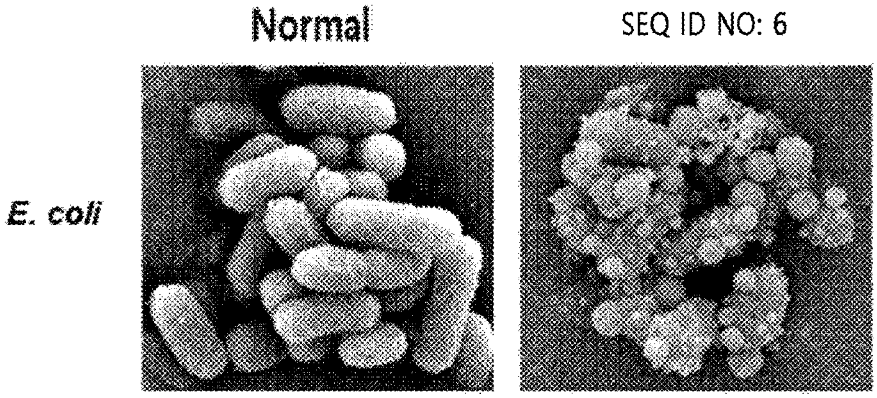

ANTIMICROBIAL PEPTIDE WITH EXCELLENT MICROBIAL CYTOPLASM ELUTION EFFECT

CROSS-REFERENCE TO RELATED APPLICATIONS

This is a National phase application under 35 U.S.C. § 371 of International Patent Application No. PCT/KR2021/016051, filed Nov. 5, 2021, which claims priority to Korean Application No. 10-2021-0011657, filed Jan. 27, 2021, both of which are incorporated herewith in their entireties.

INCORPORATION OF SEQUENCE LISTING

The Sequence Listing that is contained in the file named "OPA21332" which is 3,852 bytes and was created on Aug. 6, 2024, is filed herewith by electronic submission, and is incorporated by reference herein.

TECHNICAL FIELD

The present disclosure relates to an antimicrobial peptide, a derivative thereof, or a fragment thereof; a polynucleotide encoding the antimicrobial peptide, a derivative thereof, or a fragment thereof; and a carrier for external skin preparation, a cosmetic composition, a quasi-drug composition, and a pharmaceutical composition containing the antimicrobial peptide, a derivative thereof, or a fragment thereof.

BACKGROUND ART

Currently, the demand for products with excellent antimicrobial power is increasing in response to the pandemic era, and increasingly, various attempts to develop antimicrobial products are being made. In an effort to this end, research and development of natural antibiotics are being conducted.

Specifically, although natural product-derived antibiotics such as an antimicrobial composition containing a plant extract as an active ingredient (Korean Patent Publication No. 10-2020-0017912) are known, natural products such as extracts have large particle sizes, it is difficult to acquire significant effects from only natural products, and the need to develop antimicrobial substances has emerged.

DISCLOSURE

Technical Problem

The inventors of the present disclosure have completed the present disclosure by confirming that the antimicrobial peptide of the present disclosure is remarkably superior in antimicrobial effect compared to other peptides.

Technical Solution

An object of the present disclosure is to provide an antimicrobial peptide, a derivative thereof, or a fragment thereof.

Another object of the present disclosure is to provide a polynucleotide encoding the antimicrobial peptide, a derivative thereof, or a fragment thereof.

Still another object of the present disclosure is to provide a carrier for external skin preparation containing the antimicrobial peptide, a derivative thereof, or a fragment thereof.

Still another object of the present disclosure is to provide a cosmetic composition containing the antimicrobial peptide, a derivative thereof, or a fragment thereof.

Still another object of the present disclosure is to provide a quasi-drug composition containing the antimicrobial peptide, a derivative thereof, or a fragment thereof.

Still another object of the present disclosure is to provide a pharmaceutical composition containing the antimicrobial peptide, a derivative thereof, or a fragment thereof.

Advantageous Effects

The present disclosure has remarkably increased antimicrobial activity and decreased toxicity compared to other peptides, and can be expected to be industrially utilized in industries such as preservatives, pharmaceuticals, and cosmetics.

BRIEF DESCRIPTION OF DRAWINGS

FIGS. 1A-B are a diagram illustrating the results of confirming the antimicrobial activity and cytotoxicity of a peptide of SEQ ID NO: 1 in comparison to a known peptide;

FIGS. 2A-B are a diagram illustrating the results of confirming the antimicrobial activity and cytotoxicity of a peptide of SEQ ID NO: 2 in comparison to a peptide of SEQ ID NO: 1;

FIGS. 3A-B are a diagram illustrating the results of confirming the antimicrobial activity and cytotoxicity of peptides of SEQ ID NO: 2 and SEQ ID NO: 5 to SEQ ID NO: 8;

FIGS. 4A-B are a diagram illustrating the results of confirming the antimicrobial activity and cytotoxicity of peptides of SEQ ID NO: 2 to SEQ ID NO: 4;

FIG. 5 is a diagram illustrating the results of confirming the antimicrobial effect of an antimicrobial peptide of the present disclosure against *Escherichia coli, Staphylococcus aureus, Pseudomonas aeruginosa*, and *Candida albicans*; and FIG. 6 is a diagram illustrating the results of analyzing the antimicrobial effect of an antimicrobial peptide of the present disclosure against *Escherichia coli* using a scanning electron microscope (SEM).

DETAILED DESCRIPTION OF THE INVENTION

Hereinafter, the contents of the present disclosure will be described in detail as follows. Meanwhile, the description and embodiment of an aspect disclosed in the present disclosure may also be applied to the description and embodiment of another aspect with respect to common matters. Additionally, all combinations of the various elements disclosed herein fall within the scope of the present disclosure. In addition, it cannot be seen that the scope of the present disclosure is limited by the specific descriptions described below.

An aspect of the present disclosure provides an antimicrobial peptide consisting of any one of amino acid sequences of SEQ ID NO: 5 to SEQ ID NO: 8, a derivative thereof, or a fragment thereof.

In the present disclosure, "antimicrobial peptide" means a peptide having antimicrobial activity. Since the antimicrobial activity is not limited depending on the kind of microorganism, the term "antimicrobial" may be used interchangeably with antibacterial, antifungal, and antibiotic. Specifically, the antimicrobial peptide of the present disclosure may include any one of the amino acid sequences of SEQ ID NO: 5 to SEQ ID NO: 8, and may also include a derivative of any one of SEQ ID NO: 5 to SEQ ID NO: 8 or a fragment thereof as long as it has antimicrobial activity.

The antimicrobial peptide may be a substance expressed by the innate immune system (primary defense) to protect subjects in various species such as, plants, insects, amphibians, mammals, and humans from microorganisms such as bacteria, and may have excellent antimicrobial power and little resistance compared to existing antibiotics, but is not limited thereto as long as it functions as an antimicrobial peptide.

The antimicrobial peptide of the present disclosure is not limited depending on the structure and the like as long as it has antimicrobial activity. The microorganism is not limited as long as it is included in the category of microorganisms, and may include all bacteria, fungus and the like, and is not limited depending on the kind and origin.

Specifically, an antimicrobial peptide consisting of any one of amino acid sequences of SEQ ID NO: 5 to SEQ ID NO: 8, a derivative thereof, or a fragment thereof may inhibit the growth of any one or more selected from the group consisting of *Escherichia coli, Staphylococcus aureus, Pseudomonas aeruginosa*, and *Candida albicans*, but is not limited thereto.

In Example of the present disclosure, it has been confirmed that an antimicrobial peptide consisting of any one of amino acid sequences of SEQ ID NO: 5 to SEQ ID NO: 8 and a derivative thereof has antimicrobial activity against *Escherichia coli, Staphylococcus aureus, Pseudomonas aeruginosa*, and/or *Candida albicans* (Example 2).

In the present disclosure, "derivative" means a derivative of an antimicrobial peptide consisting of any one of amino acid sequences of SEQ ID NO: 5 to SEQ ID NO: 8, specifically may be a peptide having an amino acid sequence in which some functional group(s) is/are added to the amino acid sequences of SEQ ID NO: 5 to SEQ ID NO: 8 or some amino acid sequence(s) is/are deleted, modified, substituted, or added, but is not limited thereto.

Specifically, the derivative in the present disclosure may be any one or more selected from the group consisting of SEQ ID NO: 1 to SEQ ID NO: 4, may function as an antimicrobial peptide as the antimicrobial peptides consisting of the amino acid sequences of SEQ ID NO: 5 to SEQ ID NO: 8 do, and the antimicrobial peptides are as described above.

The antimicrobial peptides consisting of the amino acid sequences of SEQ ID NO: 5 to SEQ ID NO: 8 and derivatives thereof of the present disclosure may have antimicrobial activity while having a sequence as represented by the following Chemical Formula 1, but are not limited thereto.

$[X_1—X_2$-Leu-Phe-$X_3—X_4$-Ile-Leu-$X_5$-Tyr-Leu-$X_6]$ [Chemical Formula 1]

In Chemical Formula 1, $X_1$ to $X_6$ may be selected from basic amino acids, and may be selected from arginine, lysine, leucine, and phenylalanine. Preferably, the antimicrobial peptide consisting of any one of the amino acid sequences of SEQ ID NO: 5 to SEQ ID NO: 8 and a derivative thereof may have the sequence represented by Chemical Formula 1, and the derivative of the present disclosure may consist of the amino acid sequences of SEQ ID NO: 1 to SEQ ID NO: 4, but is not limited thereto.

SEQ ID NO: 1:
$H_2N$-[[Lys-Lys-Leu-Phe-Lys-Lys-Ile-Leu-Lys-Tyr-Leu-Lys]]-$CO_2H$,

SEQ ID NO: 2:
$H_2N$-[[Arg-Arg-Leu-Phe-Arg-Arg-Ile-Leu-Arg-Tyr-Leu-Arg]]-$CO_2H$,

SEQ ID NO: 3:
$H_2N$-[[Arg-Phe-Leu-Phe-Arg-Leu-Ile-Leu-Arg-Tyr-Leu-Arg]]-$CO_2H$,

SEQ ID NO: 4:
$H_2N$-[[Arg-Arg-Leu-Phe-Arg-Leu-Ile-Leu-Arg-Tyr-Leu-Phe]]-$CO_2H$,

SEQ ID NO: 5:
$H_2N$-[[Arg-Lys-Leu-Phe-Lys-Arg-Ile-Leu-Arg-Tyr-Leu-Lys]]-$CO_2H$,

SEQ ID NO: 6:
$H_2N$-[[Lys-Arg-Leu-Phe-Arg-Lys-Ile-Leu-Lys-Tyr-Leu-Arg]]-$CO_2H$,

SEQ ID NO: 7:
$H_2N$-[[Lys-Arg-Leu-Phe-Lys-Arg-Ile-Leu-Arg-Tyr-Leu-Lys]]-$CO_2H$,
and SEQ ID NO: 8:
$H_2N$-[[Arg-Lys-Leu-Phe-Arg-Lys-Ile-Leu-Lys-Tyr-Leu-Arg]]-$CO_2H$ Specifically, the derivative may be one in which the amino acid corresponding to any one position selected from the group consisting of the 1st, 2nd, 5th, 6th, 9th, and 12th positions from the N-terminus of the antimicrobial peptide consisting of any one of the amino acid sequences of SEQ ID NO: 5 to SEQ ID NO: 8 is substituted with another basic amino acid.

Amino acid substitution may generally occur based on the polarity, charge, solubility, hydrophobicity, hydrophilicity and/or amphipathic nature of the residues. Specifically, among electrically charged amino acids, positively charged (basic) amino acids include arginine (R), lysine (K), and histidine (H) and negatively charged (acidic) amino acids include glutamate (E) and aspartate (D); and among uncharged amino acids, nonpolar amino acids include glycine (G), alanine (A), valine (V), leucine (L), isoleucine (I), methionine (M), phenylalanine (F), tryptophan (W), and proline (P), polar or hydrophilic amino acids include serine (S), threonine (T), cysteine (C), tyrosine (Y), asparagine (N), and glutamine (Q), and aromatic amino acids among the nonpolar amino acids include phenylalanine, tryptophan, and tyrosine.

In the present disclosure, "substitution with another basic amino acid" is not limited as long as it is substitution with a basic amino acid different from the amino acid before substitution. In other words, the substitution may be substitution of the amino acid before substitution, which is present at any one position selected from the group consisting of the 1st, 2nd, 5th, 6th, 9th, and 12th positions from the N-terminus of the antimicrobial peptide consisting of any one of the amino acid sequences of SEQ ID NO: 5 to SEQ ID NO: 8, with another basic amino acid, and specifically may be substitution of an amino acid present at any one position selected from the group consisting of the $X_1$, $X_2$, $X_3$, $X_4$, $X_5$, and $X_6$ positions with another basic amino acid. Specifically, the basic amino acid may be selected from histidine, lysine, or arginine, and may be lysine or arginine, but is not limited thereto.

For the purpose of the present disclosure, the derivative of the antimicrobial peptide consisting of any one of the amino acid sequences of SEQ ID NO: 5 to SEQ ID NO: 8 may be any one or more selected from the group consisting of SEQ ID NO: 1 to SEQ ID NO: 4, but is not limited thereto.

In Example of the present disclosure, it has been confirmed that peptides of SEQ ID NO: 5 to SEQ ID NO: 8 and derivatives thereof, the peptides of SEQ ID NO: 1 to SEQ ID NO: 4, have the structure represented by Chemical Formula 1 and have antimicrobial activity (Example 2).

Specifically, in Example of the present disclosure, it has been confirmed that the antimicrobial activity of the antimicrobial peptide consisting of the amino acid sequence represented by Chemical Formula 1 or a derivative thereof is excellent, and it has been confirmed that the antimicrobial activity of more specifically SEQ ID NO: 1, SEQ ID NO: 2, and SEQ ID NO: 5 to SEQ ID NO: 8, still more specifically SEQ ID NO: 5 to SEQ ID NO: 8, particularly specifically SEQ ID NO: 6 is remarkably excellent (Example 1 and Example 2).

In the present disclosure, "fragment" refers to a partial sequence of a peptide having a specific sequence, may be a partial sequence of an antimicrobial peptide consisting of any one of the amino acid sequences of SEQ ID NO: 5 to SEQ ID NO: 8 or a derivative thereof, and may have antimicrobial activity as the antimicrobial peptide or derivative thereof does.

The antimicrobial peptide consisting of any one of the amino acid sequences of SEQ ID NO: 5 to SEQ ID NO: 8, a derivative thereof, or a fragment thereof may be derived from a natural product, but is not limited thereto, and a sequence having the same activity as that of the antimicrobial peptide, a derivative thereof, or a fragment thereof may be included without limitation.

The antimicrobial peptide in the present disclosure is described as an antimicrobial peptide consisting of any one of the amino acid sequences of SEQ ID NO: 5 to SEQ ID NO: 8, a derivative thereof, or a fragment thereof, but does not exclude meaningless sequence additions before and after the amino acid sequence of the antimicrobial peptide consisting of any one of the amino acid sequences of SEQ ID NO: 5 to SEQ ID NO: 8, a derivative thereof, or a fragment thereof or silent mutation that enable the antimicrobial peptide to maintain the same function as an antimicrobial peptide, and it may be apparent to those skilled in the art that those having the same or equivalent activity as that of the antimicrobial peptide consisting of any one of the amino acid sequences of SEQ ID NO: 5 to SEQ ID NO: 8, a derivative thereof, or a fragment thereof correspond to the antimicrobial peptide of the present disclosure. As a specific example, the antimicrobial peptide of the present disclosure may be an antimicrobial peptide consisting of any one of the amino acid sequences of SEQ ID NO: 5 to SEQ ID NO: 8, a derivative thereof, a fragment thereof, or a peptide consisting of an amino acid sequence having 80%, 90%, 95%, 96%, 97%, 98%, or 99% or more homology or identity thereto.

In the present disclosure, even when it is described as "peptide containing an amino acid sequence described as a specific sequence number", "peptide consisting of an amino acid sequence described as a specific sequence number", or "peptide having an amino acid sequence described as a specific sequence number", it is apparent that peptides having amino acid sequences in which some sequences are deleted, modified, substituted, conservatively substituted or added may also be used in the present disclosure as long as the peptides has the same or equivalent activity as that of the peptide consisting of the amino acid sequence of the corresponding sequence number. Examples thereof include peptides having a sequence addition that does not alter the function of the peptide at the N-terminus and/or C-terminus of the amino acid sequence, a mutation that may occur naturally, a silent mutation thereof, or a conservative substitution.

The "conservative substitution" means the substitution of one amino acid with another amino acid having similar structural and/or chemical properties. Such amino acid substitution may generally occur based on similarities in polarity, charge, solubility, hydrophobicity, hydrophilicity and/or amphipathic nature of the residues. Typically, conservative substitution has little or no effect on the activity of peptide.

The peptide of the present disclosure may be prepared by consecutively forming an amide bond between one or more amino acids or appropriately protected amino acids and an amino acid backbone constantly bonded to a solid phase, bur is not limited thereto. The peptide can be inserted, substituted, or deleted with other amino acids within a range that does not remarkably deteriorate the stability, and this also falls within the scope of the present disclosure.

The peptide of the present disclosure may be prepared in a form in which a cell permeable peptide that promotes intracellular migration is bonded to the C-terminus or the N-terminus. For example, the cell permeable peptide may be a TAT peptide (Arg-Lys-Lys-Arg-Arg-Tyr-Arg-Arg-Arg) and a Tat-PTD peptide (Gly-Arg-Lys-Lys-Arg-Arg-Gln-Arg-Arg-Arg: Tat-PTD), but the present disclosure is not limited thereto, and any cell permeable peptide known in the art can be used as long as it does not inhibit the activity of the peptide according to the present disclosure.

The peptide and compound of the present disclosure may be prepared in the form of metal complexes, and the metal may be selected from copper, magnesium, calcium, iron, zinc, nickel, silver, germanium, and gallium, but is not limited thereto, and copper may be preferably used, but the metal is not limited thereto.

Meanwhile, the peptide of the present disclosure may exist in the form of a salt. The form of the salt usable in the present disclosure may be formed during the final separation and purification of the compound or by reacting an amino group with an appropriate acid. For example, acid addition salts may be acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethanesulfonate, lactate, maleate, mesitylene sulfonate, methanesulfonate, naphthylenesulfonate, nicotinate, 2-naphthalenesulfonate, oxalate, pamoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate, but are not limited thereto. Examples of acids that can be used to form acid addition salts include inorganic acids such as hydrochloric acid, hydrobromic acid, sulfuric acid, and phosphoric acid; and organic acids such as oxalic acid, maleic acid, succinic acid, and citric acid, but are not limited thereto. Preferably, the peptide of the present disclosure may be prepared in the form of trifluoroacetate salt or acetate salt.

The amino group or carboxyl group of an amino acid used for preparing the peptide contained in the composition of the present disclosure may be protected by a suitable protecting group. The protected amino acid may undergo a reaction in a solution by being attached to a solid support or by adding the next amino acid under conditions suitable to form an amide bond. The protecting group may be completely removed prior to addition of the amino acid protected with a suitable protecting group. After all amino acids have been linked as desired, the amino acids may be sequentially or simultaneously separated from the freed residual protecting group and the freed solid support to obtain the final desired peptide.

As the most preferred synthesis method for preparing the peptide compound of the present disclosure, a solid phase peptide synthesis method in which synthesis is performed using a solid phase polymer support may be used, and the α-amino group of the peptide prepared through the method may be protected by an acid or base sensitive functional group. At this time, the protecting group of the amino acid is required to have the property of being stable under the conditions for the condensation reaction to form a peptide, and is required to have the property of being readily removable without breaking the elongated peptide chain or without racemization of any chiral center contained therein. Hence, suitable protecting groups may be 9-fluorenylmethyloxycarbonyl (Fmoc), t-butoxycarbonyl (Boc), benzyloxycarbonyl (Cbz), biphenylisopropyl-oxycarbonyl, t-amyloxycarbonyl, isobornyl oxycarbonyl, (α,α)-dimethyl-3,5-dimethoxybenzyloxycarbonyl, O-nitrophenylsulfenyl, 2-cyano-t-butyloxycarbonyl and the like, and other suitable protecting groups known in the art may also be used for this purpose within the scope of the present disclosure.

A 9-fluorenylmethyloxycarbonyl (Fmoc) protecting group may be used as the most preferred protecting group for amino acids used in the peptide synthesis of the present disclosure.

In particular, as the protecting groups for the amino acid residues used in the peptide synthesis of the present disclosure, t-butyl (t-Bu) is preferred for N-methylglutamic acid; t-butoxycarbonyl (Boc) for lysine; t-butyl (t-Bu) for serine; t-butyl (t-Bu) for threonine and allothreonine; and trityl (Trt) for cysteine, but the present disclosure is not limited thereto.

In the solid phase peptide synthesis method, the C-terminal amino acid can be attached to a suitable solid support or resin. The suitable solid support useful for the synthesis is preferably substances that are inert to the reagents and reaction conditions for the stepwise condensation-deprotection reaction and insoluble in the medium used, and may be, for example, 2-chlorotrityl chloride resin, rink amide, or rink amide 4-methylbenzylhydrylamine resin (rink amid MBHA resin).

In particular, preferred solid supports for C-terminal peptides may be 2-chlorotrityl chloride, rink amide or rink amide 4-methylbenzylhydrylamine resin (rink amid MBHA resin) commercially available from Novabiochem Corporation.

The C-terminal amide may be condensed (bonded, coupled) to a resin or solid phase support through condensation by activating N,N-dicyclohexylcarbodiimide (DCC), N, N-diisopropylcarbodiimine (DIC), [hexafluorophosphate O-(7-azabenzotriazol-1-yl)-1,1,3,3-tetramethyluronium] (HATU) or hexafluorophosphate O-benzotriazol-1-yl-N,N, N, N-tetramethyluronium (HBTU) with carboxylic acid in the presence or absence of 4-dimethylaminopyridine (DMAP), 1-hydroxybenzotriazole (HOBt), N-methylmorpholine (NMM), benzotriazol-1-yloxy-tris (dimethylamino) phosphonium-hexafluorophosphate (BOP) or bis(2-oxo-3-oxazolidinyl)phosphinic chloride (BOPCl) in a solvent such as dichloromethane, N-methylpyridone (NMP) or DMF at a temperature of 10° C. to 50° C., preferably at a temperature of 30° C. for 1 to 24 hours.

When the solid support is a rink amide 4-methylbenzylhydrylamine resin, the Fmoc functional group as a preferred protecting group is cleaved using an excess of a secondary amine solution, preferably a 20% solution of piperidine in DMF, prior to condensation with the C-terminal amino acid. Preferred reagents used for condensation of the desired amino acid to the deprotected 4-(2',4'-dimethoxyphenyl-Fmoc-aminomethyl) phenoxyacetamidoethyl resin are reagents for condensation reaction such as N-methylmorpholine (NMM), 1-hydroxybenzotriazole (HOBt) and [hexafluorophosphate O-(7-azabenzotriazol-1-yl)-1,1,3,3-tetramethyluronium] (HATU), hexafluorophosphate O-benzotriazol-1-yl-N,N,N, N-tetramethyluronium (HBTU), N,N-dicyclohexylcarbodiimide (DCC) or N,N-diisopropylcarbodiimide (DIC) in DMF solvent for suitably protected amino acids.

The consecutive condensation of amino acids performed in the present disclosure may be conducted directly using an automatic peptide synthesizer widely known in the related art or manually. As preferred conditions for the synthesis reaction, the α-amino acid protected with the Fmoc group may be deprotected by treatment with a secondary amine solution, preferably piperidine and then washed with a sufficient excess of solvent, other respective protected amino acids to be condensed may be subsequently added in a 3- to 7-fold molar excess, and the reaction may be conducted preferably in DMF solvent.

In the final stage of peptide synthesis using a solid-state resin of the present disclosure, the peptide to be obtained may be removed from the resin continuously or in a single operation, and the protecting groups protecting the respective amino acid residues may be deprotected. As conditions for removing the peptide from the resin and deprotecting the protecting groups present in the residues, a cocktail of cleavage reagents that typically cleave resin-peptide bonds, for example, a dichloromethane mixed cocktail solution containing trifluoroacetic acid (TFA), triisopropylsilane (TIS), thioanisole, water or ethanedithiol (EDT) etc. may be used for the treatment. The mixed solution obtained in this way may be treated with an excess of diethyl ether solvent stored in a refrigerator to form a precipitate. The precipitate obtained as described above is completely precipitated by centrifugation, and the excess of trifluoroacetic acid, triisopropylsilane, thioanisole, water, ethanedithiol, and the like are first removed, and this procedure is repeated two or more times, whereby a solidified precipitate may be obtained. At this time, the completely deprotected peptide salt may be separated and purified using a mixed solvent composed of water and acetonitrile solvent and reverse phase high performance liquid chromatography (HPLC). The separated and purified peptide solution may be completely concentrated and dried by lyophilization to obtain a solid peptide.

Another aspect of the present disclosure provides a polynucleotide encoding an antimicrobial peptide consisting of any one of amino acid sequences of SEQ ID NO: 5 to SEQ ID NO: 8, a derivative thereof, or a fragment thereof.

Any one of the amino acid sequences of SEQ ID NO: 5 to SEQ ID NO: 8, and the antimicrobial peptide, derivative, and fragment are as described above.

Specifically, the antimicrobial peptide consisting of any one of amino acid sequences of SEQ ID NO: 5 to SEQ ID NO: 8 may consist of the sequence represented by Chemical Formula 1, and the derivative may consist of any one sequence selected from the group consisting of SEQ ID NO: 1 to SEQ ID NO: 4, but the present disclosure is not limited thereto.

The antimicrobial peptide, a derivative thereof, or a fragment thereof may be encoded by any one sequence selected from the group consisting of SEQ ID NO: 9 to SEQ ID NO: 16, but is not limited thereto.

In the present disclosure, the amino acid sequences of SEQ ID NO: 5 to SEQ ID NO: 8 or derivatives thereof may be encoded by, for example, polynucleotides containing nucleic acid sequences of SEQ ID NO: 9 to SEQ ID NO: 16.

In the present disclosure, "polynucleotide" is a polymer of nucleotides in which nucleotide monomers are connected in a long chain shape by covalent bonds, and means a DNA or RNA strand of a certain length or more. In the present disclosure, the polynucleotide may encode a peptide exhibiting the activity of antimicrobial peptides having amino acid sequences of SEQ ID NO: 5 to SEQ ID NO: 8, derivatives thereof, or fragments thereof, but is not limited thereto.

The polynucleotide may include without limitation any polynucleotide encoding a peptide having the activity of the antimicrobial peptide according to the present disclosure, a derivative thereof, or a fragment thereof.

Specifically, the polynucleotide encoding a peptide exhibiting the activity of the antimicrobial peptide, a derivative thereof, or a fragment thereof may include a nucleic acid sequence encoding an amino acid described as Chemical Formula 1, the antimicrobial peptide, a derivative thereof, or a fragment thereof. Various modifications may be made to the coding region of the polynucleotide due to codon degeneracy or in consideration of codons preferred in organisms intended to express the peptide within the range of not changing the amino acid sequence of the peptide. The polynucleotide may include, for example, nucleic acid sequences of SEQ ID NO: 9 to SEQ ID NO: 16, and may consist of a nucleic acid sequence having 80% or more, specifically 90% or more, more specifically 95% or more, 96% or more, 97% or more, 98% or more, or still more specifically 99% or more homology or identity thereto, but is not limited thereto.

The polynucleotide of the present disclosure may be hybridized with a probe, for example, a sequence complementary to all or part of the nucleic acid sequence under stringent conditions to include without limitation any sequence encoding the amino acid sequences of SEQ ID NO: 5 to SEQ ID NO: 8, derivatives thereof, or fragments thereof. The "stringent condition" means conditions that allow specific hybridization between polynucleotides. These conditions are specifically described in literatures (for example, J. Sambrook et al.). Examples thereof include conditions in which polynucleotides having high homology or identity, namely, polynucleotides having 40% or more, specifically 90% or more, more specifically 95% or more, 96% or more, 97% or more, 98% or more, or still more specifically 99% or more homology or identity hybridize with each other and polynucleotides having homology or identity lower than this do not hybridize with each other; or conditions in which washing is performed 1 time, specifically 2 to 3 times at a salt concentration and temperature corresponding to 60° C., 1×SSC, and 0.1% SDS, specifically 60° C., 0.1×SSC, and 0.1% SDS, more specifically 68° C., 0.1×SSC, and 0.1% SDS, which are washing conditions for conventional southern hybridization.

Hybridization requires that two nucleic acids have complementary sequences although mismatches between bases are possible depending on the stringency of hybridization. The term "complementary" is used to describe the relation between nucleotide bases capable of hybridizing with each other. For example, with regard to DNA, adenine is complementary to thymine and cytosine is complementary to guanine. Hence, the polynucleotide of the present disclosure may also include substantially similar nucleic acid sequences as well as isolated nucleic acid fragments complementary to the entire sequence.

Specifically, polynucleotides having homology or identity may be detected using hybridization conditions including a hybridization step at a $T_m$ value of 55° C. and using the above-described conditions. The $T_m$ value may be 60° C., 63° C., or 65° C., but is not limited thereto, and may be appropriately adjusted by those skilled in the art according to the purpose.

Appropriate stringency for hybridizing polynucleotides depends on the length and degree of complementarity of the polynucleotides, and the parameters are well known in the art (see Sambrook et al., supra, 9.50-9.51, 11.7-11.8).

In the present disclosure, the term "homology" or "identity" refers to the degree of association between two given amino acid sequences or nucleic acid sequences and may be expressed as a percentage. The terms homology and identity are often used interchangeably.

Sequence homology or identity of conserved polynucleotides or peptides is determined by standard alignment algorithms, and default gap penalties established by the program being used may be used together. Substantially homologous or identical sequences are generally capable of hybridizing under moderate or highly stringent conditions along all or at least about 50%, 60%, 70%, 80%, or 90% of the full-length sequence. It is obvious that hybridization also includes polynucleotides containing common codons or codons considering codon degeneracy in polynucleotides.

Whether any two polynucleotide or peptide sequences have homology, similarity or identity may be determined using known computer algorithms such as the "FASTA" program, for example, using the same default parameters as in Pearson et al., (1988) *Proc. Natl. Acad. Sci. USA* 85:2444. Alternatively, the homology, similarity, or identity may be determined using the Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000, *Trends Genet.* 16:276-277) (version 5.0.0 or later) (including the GCG program package (Devereux, J., et al, *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, BLAST of the National Center for Biotechnology Information Database, or ClustalW may be used to determine homology, similarity, or identity.

Homology, similarity, or identity of polynucleotides or peptides may be determined by comparing sequence information using, for example, a GAP computer program such as Needleman et al. (1970), *J Mol Biol.* 48:443, as noted in, for example, Smith and Waterman, *Adv. Appl. Math* (1981) 2:482. In summary, using the GAP program, the homology, similarity, or identity may be defined by the value acquired by dividing the number of similarly aligned symbols (namely, nucleotides or amino acids) by the total number of symbols in the shorter of the two sequences. The default parameters for the GAP program include (1) a binary comparison matrix (containing values of 1 for identity and 0 for non-identity) and a weighted comparison matrix of Gribskov et al. (1986) *Nucl. Acids Res.* 14:6745 (or EDNA-FULL (EMBOSS version of NCBI NUC4.4) substitution matrix) as disclosed by Schwartz and Dayhoff, eds., *Atlas Of Protein Sequence And Structure*, National Biomedical Research Foundation, pp. 353-358 (1979); (2) a penalty of 3.0 for each gap and an additional penalty of 0.10 for each symbol in each gap (or 10 gap opening penalty, 0.5 gap extension penalty); and (3) no penalty for end gaps.

Whether any two polynucleotide or peptide sequences have homology, similarity or identity may be confirmed by comparing the sequences by Southern hybridization experiments under defined stringent conditions. The appropriate hybridization conditions to be defined are within the skill of the art and may be determined by methods well known to those skilled in the art (for example, J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

Still another aspect of the present disclosure provides a carrier for external skin preparation containing an antimicrobial peptide consisting of any one of amino acid sequences of SEQ ID NO: 5 to SEQ ID NO: 8, a derivative thereof, or a fragment thereof.

Any one of the amino acid sequences of SEQ ID NO: 5 to SEQ ID NO: 8, and the antimicrobial peptide, derivative, and fragment are as described above. In the present disclosure, "carrier" means one that can support any substance or component and is exemplified by a composition, and may be used interchangeably with a carrying agent, an impregnating agent, or a mediator. The composition, which is an example of the carrier, may be applied and delivered to the skin through an application means such as a hand, puff, tip, or brush.

The carrier may be contained in a cosmetic composition, a pharmaceutical composition, or a quasi-drug composition, but is not limited thereto. For the purpose of the present disclosure, the carrier may contain antimicrobial peptides consisting of amino acid sequences of SEQ ID NO: 5 to SEQ ID NO: 8, derivatives thereof, or fragments thereof.

In the present disclosure, "external skin preparation" means a formulation applied to the skin. In the present disclosure, the shape and the like of the external preparation are not limited as long as the external preparation is a formulation applied to the skin, and the external preparation may be further classified into ointments, creams, lotions, gels, and the like, but is not limited thereto.

Specifically, the ointment may be a semi-solid external preparation in which the main component applied to the skin is dissolved or dispersed in a base. The base may be divided into oil and fat ointments and water-soluble ointments depending on the component. Ointments using an oleaginous base may have a skin softening action, have excellent sealability and are suitable for application to wounds, but have a disadvantage of not being easily removed. Ointments using an oleaginous base may be an advantageous formulation when locally permeating components that hardly permeate the skin because of skin-like fat-soluble properties and skin softening action.

The ointment is generally composed of an oil phase such as oil, and so is excellent in moisturization and favorable for permeation of fat-soluble components, but has a disadvantage of being sticky. The cream may be a semi-solid external preparation emulsified in a water-in-oil type, and may be a formulation in which the stickiness of ointments is improved by mixing an oil phase with a water phase. As an emulsification process, mixing may be performed using a surfactant or through a special process to mix the oil phase with the water phase. The cream may be a formulation that is more easily applied and removed than an ointment, and a lotion is a formulation having more water-like properties than a cream, and may be an external preparation in which the main component is dissolved, emulsified, or finely dispersed in an aqueous liquid. The lotion may be a solution, suspension, or emulsion made homogeneous using the main component, additives, and purified water. The gel may be a semi-solid external preparation composed of organic molecules with a high molecular weight penetrated by liquid. In the gel, a gelling agent may be dispersed in an aqueous solution, and a gelling agent such as carbomer or synthetic polymer may be used. Various kinds of solvents may be used depending on the active ingredient, purpose of use, method of use, and the like, and the external preparation of the present disclosure is not limited thereto.

Still another aspect of the present disclosure provides a cosmetic composition containing an antimicrobial peptide consisting of any one of amino acid sequences of SEQ ID NO: 5 to SEQ ID NO: 8, a derivative thereof, or a fragment thereof.

Any one of the amino acid sequences of SEQ ID NO: 5 to SEQ ID NO: 8, and the antimicrobial peptide, derivative, and fragment are as described above.

In the present disclosure, the cosmetic composition may be prepared in a formulation selected from the group consisting of solutions, external ointments, creams, foams, nutrient lotions, softening lotions, perfumes, packs, softening waters, milky lotions, makeup bases, essences, liquid cleansers, bath additives, sunscreen creams, sun oils, suspensions, emulsions, pastes, gels, lotions, powders, soaps, surfactant-containing cleansings, oils, powder foundations, emulsion foundations, wax foundations, patches, and sprays, but is not limited thereto.

The cosmetic composition of the present disclosure may further contain one or more cosmetically acceptable carriers blended in general skin cosmetics, and for example, oil component, water, surfactants, moisturizers, lower alcohols, thickeners, chelating agents, colorants, preservatives, fragrances, and the like may be appropriately blended as usual components, but cosmetic composition is not limited thereto.

The cosmetically acceptable carriers contained in the cosmetic composition of the present disclosure vary depending on the formulation of the cosmetic composition.

When the formulation of the present disclosure is an ointment, paste, cream or gel, animal oils, vegetable oils, waxes, paraffin, starch, tragacanth, cellulose derivatives, polyethylene glycol, silicone, bentonite, silica, talc, zinc oxide, and the like may be used as the carrier components, but the carrier components are not limited thereto. These may be used singly or in a mixture of two or more kinds thereof.

When the formulation of the present disclosure is a powder or spray, lactose, talc, silica, aluminum hydroxide, calcium silicate, polyamide powder, and the like may be used as the carrier components, particularly in the case of a spray, a propellant such as chlorofluorohydrocarbons, propane/butane, or dimethyl ether may be additionally contained, but the carrier components are not limited thereto. These may be used singly or in a mixture of two or more kinds thereof.

When the formulation of the present disclosure is a solution or emulsion, a solvent, a solubilizing agent, or an emulsifying agent may be used as the carrier components, for example, water, glycerin, ethanol, isopropanol, ethyl carbonate, ethyl acetate, benzyl alcohol, benzyl benzoate, propylene glycol, 1,3-butyl glycol oil, and the like may be used, particularly cottonseed oil, peanut oil, corn germ oil, olive oil, castor oil and sesame oil, glycerol fatty esters, and fatty acid esters of polyethylene glycol or sorbitan may be used, but the carrier components are not limited thereto. These may be used singly or in a mixture of two or more kinds thereof.

When the formulation of the present disclosure is a suspension, a liquid diluent such as water, glycerin, ethanol, or propylene glycol; suspending agents such as isostearyl alcohol ethoxylated, polyoxyethylene sorbitol esters, and polyoxyethylene sorbitan esters; microcrystalline cellulose, aluminum metahydroxide, bentonite, agar or tragacanth may be used as the carrier components, but the carrier components are not limited thereto. These may be used singly or in a mixture of two or more kinds thereof.

When the formulation of the present disclosure is a soap, alkali metal salts of fatty acids, fatty acid hemiester salts, fatty acid protein hydrolysates, isethionates, lanolin derivatives, fatty alcohols, vegetable oils, glycerol, sugars, and the like may be used as the carrier components, but the carrier components are not limited thereto. These may be used singly or in a mixture of two or more kinds thereof.

Still another aspect of the present disclosure provides a quasi-drug composition containing an antimicrobial peptide consisting of any one of amino acid sequences of SEQ ID NO: 5 to SEQ ID NO: 8, a derivative thereof, or a fragment thereof.

Any one of the amino acid sequences of SEQ ID NO: 5 to SEQ ID NO: 8, and the antimicrobial peptide, derivative, and fragment are as described above.

In the present disclosure, "quasi-drug" refers to items with milder action than pharmaceuticals among items used for the purpose of diagnosing, treating, improving, mitigating, healing, or preventing human or animal diseases. For example, according to the Pharmaceutical Affairs Act, quasi-drugs are items excluding items used for pharmaceutical purposes, and include products used for the treatment or prevention of human/animal diseases, products with minor action or no direct action on the human body, and the like.

The quasi-drug composition of the present disclosure may be prepared in a formulation selected from the group consisting of body cleansers, foams, soaps, masks, ointments, creams, lotions, essences, and sprays, but is not limited thereto.

In the cosmetic composition or quasi-drug composition of the present disclosure, the antimicrobial peptide consisting of any one of amino acid sequences of SEQ ID NO: 5 to SEQ ID NO: 8, a derivative thereof, or a fragment thereof may be contained at 0.01% to 100.0% by weight or 0.1% to 10% by weight in the total composition.

Still another aspect of the present disclosure provides a pharmaceutical composition for external skin preparation containing an antimicrobial peptide consisting of any one of amino acid sequences of SEQ ID NO: 5 to SEQ ID NO: 8, a derivative thereof, or a fragment thereof.

Any one of the amino acid sequences of SEQ ID NO: 5 to SEQ ID NO: 8, and the antimicrobial peptide, derivative, fragment, and external skin preparation are as described above.

The pharmaceutical composition of the present disclosure may further contain a pharmaceutically acceptable carrier in addition to the antimicrobial peptides consisting of amino acid sequences of SEQ ID NO: 5 to SEQ ID NO: 8, derivatives thereof, or fragments thereof.

In the present disclosure, the "pharmaceutically acceptable" means that the substance does not stimulate organisms when administered as well as does not inhibit the biological activity and properties of the administered compound, and can be commonly used in the pharmaceutical field. The pharmaceutical composition of the present disclosure may be formulated together with the carrier and utilized as a food, medicine, feed additive, drinking water additive, or the like.

The kind of carrier is not particularly limited, and any carrier commonly used in the art may be used. Non-limiting examples of the carrier include saline, sterile water, Ringer's solution, buffered saline, albumin, lactose, dextrose, sucrose, sorbitol, mannitol, xylitol, erythritol, maltitol, maltodextrin, glycerol, and ethanol. These may be used singly or in a mixture of two or more kinds thereof, but the carrier is not limited thereto.

If necessary, other pharmaceutically acceptable additives such as excipients, diluents, antioxidants, buffers or bacteriostats may be added to the pharmaceutical composition of the present disclosure for use, and fillers, extenders, wetting agents, disintegrants, dispersants, surfactants, binders, or lubricants may be additionally added to the pharmaceutical composition of the present disclosure for use, but the pharmaceutical composition is not limited thereto.

The pharmaceutical composition of the present disclosure may be prepared and used in various formulations suitable for external skin preparations.

Non-limiting examples of the external skin preparation include aerosols, sprays, cleansers, ointments, powders for application, oils, creams, and the like, and the external skin preparation is not limited thereto as long as it can function as an external skin preparation.

In order to prepare the pharmaceutical composition of the present disclosure for external skin preparations, sterilized aqueous solutions, non-aqueous solvents, suspending agents, emulsions, freeze-dried preparations, external preparations, and the like may be used, and propylene glycol, polyethylene glycol, vegetable oils such as olive oil, and esters such as ethyl oleate may be used as the non-aqueous solvent and suspending agent, but the pharmaceutical composition is not limited thereto.

More specifically, when the pharmaceutical composition of the present disclosure is prepared, the pharmaceutical composition of the present disclosure may be mixed together with a stabilizer or buffer in water to prepare a solution or suspension, and this may be prepared in units such as ampoules. When the pharmaceutical composition of the present disclosure is prepared into an aerosol, a propellant and the like may be blend with additives so that the water-dispersed concentrate or wet powder is dispersed, but the pharmaceutical composition is not limited thereto.

When the pharmaceutical composition of the present disclosure is prepared into an ointment, cream, or the like, animal oils, vegetable oils, waxes, paraffin, starch, tragacanth, cellulose derivatives, polyethylene glycol, silicone, bentonite, silica, talc, zinc oxide, and the like may be used as a carrier, but the pharmaceutical composition is not limited thereto.

The pharmaceutical composition of the present disclosure may be prepared for external skin preparations, and more preferably may be in a formulation selected from the group consisting of gels, patches, sprays, ointments, plasters, lotions, liniments, pastes, and cataplasmas, but is not limited thereto.

The pharmaceutically effective amount of the pharmaceutical composition of the present disclosure and the effective dosage for external preparation may vary depending on the preparation method, administration method, administration time, administration route and/or the like of the pharmaceutical composition, and may vary according to various factors including the kind and degree of response to be achieved by administration of the pharmaceutical composition, the kind, age, weight, general health condition, symptom or degree of disease, sex, diet, and excretion of subject to be administered, drugs used in the subject simultaneously or at the same time, and other components of the composition; and similar factors well known in the medical field. A person of ordinary skill in the art can readily determine and prescribe an effective dosage for the desired treatment. The pharmaceutical composition of the present disclosure may be administered once a day or several times a day in a divided manner. Hence, the dosage is not intended to limit the scope of the present disclosure in any way.

In the present disclosure, administration may be administration as an external preparation, and a preferred dosage of the pharmaceutical composition of the present disclosure may be 1 mg/kg to 1,000 mg/kg per day.

The administration route and administration method of the pharmaceutical composition of the present disclosure may be each independent, and the method is not particularly limited, and any administration route and any administration method may be adopted as long as the pharmaceutical composition can reach the target area. The pharmaceutical composition may be administered in the form of an external skin preparation. Specifically, a method of applying or spraying the composition to a diseased area may be used, but the method is not limited thereto.

The pharmaceutical composition of the present disclosure may be preferably administered in a manner of being applied or sprayed, and may specifically be administered in a manner of being topically applied to areas in need of improvement of skin conditions or prevention, improvement, or treatment of skin diseases.

Still another aspect of the present disclosure provides use of the antimicrobial peptide of the present disclosure, a derivative thereof, or a fragment thereof for anti-microbe.

Being antimicrobial means exhibiting antimicrobial activity, and the antimicrobial activity is not limited depending on the kind of microorganism, and the term "antimicrobial" may be used interchangeably with antibacterial, antifungal, and antibiotic.

The antimicrobial peptide, derivative, and fragment are as described above.

Still another aspect of the present disclosure provides an antimicrobial method including treating a subject with the antimicrobial peptide of the present disclosure, a derivative thereof, or a fragment thereof.

The subject is not limited as long as it is a subject in need of antimicrobial treatment, which is treated with an antimicrobial peptide, a derivative thereof, or a fragment thereof. The treatment is spraying, application and the like and is not limited as long as it can bring the subject in need of antimicrobial treatment into contact with an antimicrobial peptide, a derivative thereof, or a fragment thereof.

The antimicrobial peptide, derivative, and fragment are as described above.

FORMS FOR IMPLEMENTATION OF THE INVENTION

Hereinafter, the present disclosure will be described in more detail through Examples. However, these Examples and Experimental Examples are intended to illustrate the present disclosure, and the scope of the present disclosure is not limited to these Examples and Experimental Examples.

Preparation Example 1: Preparation of Antimicrobial Peptides

In order to examine the function of antimicrobial peptides, peptides of SEQ ID NO: 5 to SEQ ID NO: 8, and their derivative peptides were prepared.

1-1: Synthesis of peptide of SEQ ID NO: 1

Abbreviations and names of amino acids used in the present disclosure are indicated below.

Phe: Phenylalanine/Ile: Isoleucine/Lys: Lysine/Leu: Leucine/Arg: Arginine/Tyr: Tyrosine 71.4 mg (0.10 mmol) of 2-chlorotrityl chloride resin (1.4 mmol/g loaded resin) purchased from Novabiochem corporation was weighed, the resin was solvated with 7.5 mL of methylchloride and reacted for 5 minutes, and then the methylchloride was removed.

Thereafter, Fmoc-Lys (Boc)-OH (281.1 mg, 0.60 mmol) was completely dissolved in 7.5 mL of MC solvent, 0.21 mL, 1.2 mmol of N,N-diisopropylethylamine (DIPEA) was added, and the solution was added to the resin. The reaction solution was shaken at room temperature for 12 hours, and then washing with 10 ml of DMF solvent was performed 4 times.

Thereafter, 7.5 mL of a 20% (w/v) solution of piperidine in DMF was added, and shaking was performed for 15 minutes to completely remove the 9-fluorenylmethyloxycarbonyl (Fmoc) protecting group from the substance added to the resin, and washing with 10 mL of DMF solvent was performed 4 times (10 mL per 1 time of washing, 4 times). At this stage, the deprotection reaction of the Fmoc protecting group was confirmed by performing the Kaiser test (E. Kaiser et al. *Anal. Biochem.,* 1970, 34 (2), 595-598.).

Meanwhile, Fmoc-Leu-OH (212.0 mg, 0.60 mmol), hexafluorophosphate benzotriazole tetramethyluronium (HBTU) (227.6 mg, 0.60 mmol), and hydroxybenzotriazole (HOBt) (81.0 mg, 0.6 mmol) were completely dissolved in 7.5 mL of DMF solvent, then DIPEA (0.21 mL, 1.2 mmol) was added, and the solution was added to the resin. The reaction solution was shaken at room temperature for 3 hours, and then washing was performed 4 times using 10 ml of DMF solvent per 1 time of washing. At this stage, the Kaiser test was performed to confirm the completion of the reaction.

Next, the peptide was consecutively condensed (coupled) according to the same synthesis cycle as below.

(1) Four times of washing with DMF solvent (10 mL);
(2) deprotection using 20% (w/v) solution of piperidine in DMF (7.5 mL) for 15 minutes;
(3) 4 times of washing with DMF solvent (10 mL);
(4) addition of Fmoc-amino acid, HBTU, HOBt, and DIPEA;
(5) addition of HBTU, HOBt, and DIPEA condensation reagents for amino acid activation and condensation for 3 hours;
(6) 4 times of washing with DMF solvent (10 mL);
(1) to (6) above were repeated consecutively, and at this time, Fmoc-protected amino acids (0.60 mmol) after Fmoc-Leu-OH were added to the resin reaction vessel in the order described below and condensed.
(i) Fmoc-Tyr (tBu)-OH;
(ii) Fmoc-Lys (Boc)-OH;
(iii) Fmoc-Leu-OH;
(iv) Fmoc-Ile-OH;
(v) Fmoc-Lys (Boc)-OH;

(vi) Fmoc-Lys (Boc)-OH;
(vii) Fmoc-Phe-OH;
(viii) Fmoc-Leu-OH;
(ix) Fmoc-Lys (Boc)-OH;
(x) Fmoc-Lys (Boc)-OH;

After (6) after condensation of Fmoc-Lys (Boc)-OH, finally treatment with 20% (w/v) solution of piperidine in DMF (7.5 mL) was performed, and then washing was performed 3 times using 10 mL of DMF solvent per 1 time of washing, 3 times with MC solvent, and 3 times with diethyl ether solvent.

Immediately after the completion of synthesis as described above, the resin in which the peptide was condensed was treated with a mixture (10 mL) of trifluoroacetic acid/triisopropylsilane/water (95:2.5:2.5) (10 mL) for 3 hours to cleave the peptide from the resin. A precipitate was formed by treating the mixed solution thus obtained with 100 mL of diethyl ether solvent stored in a refrigerator. The obtained precipitate was completely precipitated by centrifugation, trifluoroacetic acid was first removed, and the above procedure (step of adding 100 mL of diethyl ether solvent to wash the precipitate and performing centrifugation work to remove trifluoroacetic acid, which was attempted to be removed first) was repeated 2 times to obtain a solidified precipitate.

The precipitate (peptide) was purified over 50 minutes using a C-18 column by HPLC using a 5% to 100% acetonitrile/water concentration gradient solvent system containing 0.001% trifluoroacetic acid. The pure purified fraction was lyophilized to obtain 155 mg of antimicrobial peptide of SEQ ID NO: 1 as a white powdery trifluoroacetate salt.

```
SEQ ID NO: 1:
H2N-[[Lys-Lys-Leu-Phe-Lys-Lys-Ile-Leu-Lys-Tyr-Leu-
Lys]]-CO2H,
```

MS (ESI) m/e, $[M+H]^+$=1550.17; (155 mg)

1-2: Synthesis of Peptides of SEQ ID NO: 2 to SEQ ID NO: 8

Peptides of SEQ ID NO: 2 to SEQ ID NO: 8 were prepared through the same preparation process as in Preparation Example 1-1 except that the order of amino acids protected with Fmoc was changed.

```
SEQ ID NO: 2:
H2N-[[Arg-Arg-Leu-Phe-Arg-Arg-Ile-Leu-Arg-Tyr-Leu-
Arg]]-CO2H,
```

MS (ESI) m/e, $[M+H]^+$=1718.23; (171 mg)

```
SEQ ID NO: 3:
H2N-[[Arg-Phe-Leu-Phe-Arg-Leu-Ile-Leu-Arg-Tyr-Leu-
Arg]]-CO2H,
```

MS (ESI) m/e, $[M+H]^+$=1666.18; (166 mg)

```
SEQ ID NO: 4:
H2N-[[Arg-Arg-Leu-Phe-Arg-Leu-Ile-Leu-Arg-Tyr-Leu-
Phe]]-CO2H,
```

MS (ESI) m/e, $[M+H]^+$=1666.18; (166 mg)

```
SEQ ID NO: 5:
H2N-[[Arg-Lys-Leu-Phe-Lys-Arg-Ile-Leu-Arg-Tyr-Leu-
Lys]]-CO2H,
```

MS (ESI) m/e, $[M+H]^+$=1634.2; (153 mg)

```
SEQ ID NO: 6:
H2N-[[Lys-Arg-Leu-Phe-Arg-Lys-Ile-Leu-Lys-Tyr-Leu-
Arg]]-CO2H,
```

MS (ESI) m/e, $[M+H]^+$=1634.2; (143 mg)

```
SEQ ID NO: 7:
H2N-[[Lys-Arg-Leu-Phe-Lys-Arg-Ile-Leu-Arg-Tyr-Leu-
Lys]]-CO2H,
```

MS (ESI) m/e, $[M+H]^+$=1634.2; (132 mg)

```
SEQ ID NO: 8:
H2N-[[Arg-Lys-Leu-Phe-Arg-Lys-Ile-Leu-Lys-Tyr-Leu-
Arg]]-CO2H
```

MS (ESI) m/e, $[M+H]^+$=1634.2; (172 mg)

Example 1: Evaluation of Antimicrobial Activity and Cytotoxicity of SEQ ID NO: 5 to SEQ ID NO: 8 and Derivatives Thereof In order to confirm the function as an antimicrobial peptide of the present disclosure, antimicrobial activity and cytotoxicity were evaluated. The antimicrobial activity and cytotoxicity of the antimicrobial peptide consisting of any one amino acid sequence selected from SEQ ID NO: 5 to SEQ ID NO: 8 and its derivatives, SEQ ID NO: 1 to SEQ ID NO: 4, of the present disclosure were evaluated.

Specifically, in order to evaluate the antimicrobial activity, the antimicrobial activity against *Escherichia coli* was measured, and *Escherichia coli* was treated with antimicrobial peptides, and cell viability was measured and compared.

In order to function as an antimicrobial peptide, the peptide is required to inhibit only the survival of microorganisms and exhibit minimum cytotoxicity. Therefore, cytotoxicity to human keratinocytes was also evaluated by treating human keratinocytes with antimicrobial peptides and measuring cell viability.

Antimicrobial Activity Evaluation Method

*Escherichia coli* used in this experiment was distributed from the Korea Research Institute of Bioscience and Biotechnology, Korean Collection for Type Cultures (KTCC) and cultured using LB medium. Human keratinocytes (HaCaT) were purchased from ATCC (American Type Culture Collection, USA) and cultured in Dulbecco's modified Eagle's medium (DMEM, Gibco, USA) containing 10% fetal bovine serum (FBS, Gibco, USA) and 1% antibiotic-antimycotic (Gibco, USA) at 37° C. in a 5% $CO_2$ incubator.

In order to test the antimicrobial efficacy of antimicrobial peptides, *Escherichia coli* was cultured in LB medium for about 8 hours, and then the cultured bacteria were dispensed into a 96-well plate. Antimicrobial peptide samples at various concentrations were added into the respective wells, and incubation was performed at 37° C. for 24 hours. Absorbance was measured at 600 nm using a microplate reader, and the result was expressed as a percentage (%) with respect to that of the group not treated with the sample.

Evaluation of Cytotoxicity to Human Keratinocytes

MTT assay was performed to determine the viability of HaCaT cells against antimicrobial peptides. HaCaT cells were cultured in a 96-well plate at $2\times10^5$ cells/mL for 24 hours, then treated with samples at various concentrations, and cultured again for 24 hours. The culture medium was removed, and the cells were treated with MTT solution (0.5 mg/mL in PBS). After 4 hours, the MTT solution was removed, DMSO was added to each well, and formazan was dissolved at 37° C. for 30 minutes. Absorbance was measured at 570 nm using a microplate reader (Molecular Devices Spectra MAX, Sunnyvale, CA, USA). In all experiments, the results were statistically processed by taking the average value of 3 wells for each concentration, and expressed as a relative viability (%) with respect to that of the group not treated with the sample.

1-1: Evaluation of Antimicrobial Activity and Cytotoxicity of Antimicrobial Peptide of SEQ ID NO: 1

Among the peptides of SEQ ID NO: 1 to SEQ ID NO: 8, the antimicrobial activity and cytotoxicity of the antimicrobial peptide of SEQ ID NO: 1 were firstly measured, and the antimicrobial activity and cytotoxicity of SEQ ID NO: 1 and a known antimicrobial peptide were compared and analyzed. The sequence of the antimicrobial peptide used in this Example is as follows.

Sequence of known peptide (BP-100): KKLFK KILKY L

As a result of evaluating the antimicrobial activity against *Escherichia coli*, it has been confirmed that the antimicrobial activity of the peptide of SEQ ID NO: 1 is remarkably increased compared to that of the known peptide (FIG. 1A). In addition, it has been confirmed that the toxicity level of the peptide of SEQ ID NO: 1 to human keratinocytes is maintained at a similar level to that of the known peptide (FIG. 1B).

From the facts, it has been confirmed that SEQ ID NO: 1 has a remarkable effect as an antimicrobial peptide compared to a known peptide even though SEQ ID NO: 1 is obtained by further adding one amino acid to the sequence of the known peptide.

1-2: Evaluation of Antimicrobial Activity and Cytotoxicity of Antimicrobial Peptide of SEQ ID NO: 2

The antimicrobial activity and cytotoxicity of SEQ ID NO: 1 and SEQ ID NO: 2 were compared and analyzed.

As a result of evaluating the antimicrobial activity against *Escherichia coli*, it has been confirmed that the antimicrobial activity of the peptide of SEQ ID NO: 2 is remarkably increased compared to that of the peptide of SEQ ID NO: 1 (FIG. 2A). In addition, it has been confirmed that the toxicity level of the peptide of SEQ ID NO: 2 to human keratinocytes is maintained at a level similar to that of SEQ. ID NO: 1 peptide (FIG. 2B).

From the facts, it has been confirmed that SEQ ID NO: 2 has a remarkable effect as an antimicrobial peptide.

1-3: Evaluation of Antimicrobial Activity and Cytotoxicity of Antimicrobial Peptides of SEQ ID NO: 5 to SEQ ID NO: 8

The antimicrobial activity and cytotoxicity of antimicrobial peptides of SEQ ID NO: 5 to SEQ ID NO: 8 were compared and analyzed.

In order to evaluate the antimicrobial activity against *Escherichia coli*, MIC (minimum inhibitory concentration) and $IC_{50}$ were additionally measured in addition to the experiments conducted in Examples 1-1 and 1-2.

Specifically, an antimicrobial efficacy experiment was used as the experimental method, and the MIC and $IC_{50}$ values for the experimental results were calculated by evaluating the minimum inhibitory concentration and the 50% inhibitory concentration with the absorbance and OD value, respectively.

As a result, it has been confirmed that the antimicrobial activity of the peptides of SEQ ID NO: 5 to SEQ ID NO: 8 is superior to that of the peptide of SEQ ID NO: 2.

It has been confirmed that among these, the antimicrobial activity of the peptides of SEQ ID NO: 6 and SEQ ID NO: 8 is most remarkably excellent, followed by the antimicrobial activity of the peptides of SEQ ID NO: 5 and SEQ ID NO: 7 (FIG. 3A and Table 1).

It has been confirmed that the toxicity level of the peptides of SEQ ID NO: 5 to SEQ ID NO: 8 to human keratinocytes is remarkably lower than that of a known peptide as well as is decreased compared to that of the peptide of SEQ ID NO: 2 (FIG. 3B).

From the facts, it has been confirmed that the peptides of SEQ ID NO: 5 to SEQ ID NO: 8, particularly SEQ ID NO: 6 and SEQ ID NO: 8 have remarkable effects as antimicrobial peptides as the antimicrobial activity thereof is remarkably increased compared to that of the peptide of SEQ ID NO: 1 and the cytotoxicity thereof is remarkably decreased compared to that of the peptide of SEQ ID NO: 1.

TABLE 1

| | Sample | | | | | |
|---|---|---|---|---|---|---|
| | BP-100 | SEQ ID NO: 2 | SEQ ID NO: 5 | SEQ ID NO: 6 | SEQ ID NO: 7 | SEQ ID NO: 8 |
| MIC (μM) | 125 | 62.5 | 62.5 | 31.25 | 62.5 | 31.25 |
| $IC_{50}$ (μM) | 31 | 14 | 12 | 9 | 11 | 10 |

Comparative Example: Evaluation of Antimicrobial Activity and Cytotoxicity of Peptides of SEQ ID NO: 3 and SEQ ID NO: 4

In order to evaluate whether peptides with similar sizes and similar sequences all have the same antimicrobial activity, the antimicrobial activity and cytotoxicity of SEQ ID NO: 3 and SEQ ID NO: 4 were analyzed in comparison to SEQ ID NO: 2.

As a result of evaluating the antimicrobial activity against *Escherichia coli*, it has been confirmed that the antimicrobial activity of the peptide of SEQ ID NO: 2 is remarkably excellent compared to that of the peptides of SEQ ID NO: 3 and SEQ ID NO: 4 (FIG. 4A). In addition, it has been confirmed that the toxicity level of the peptide of SEQ ID NO: 2 to human keratinocytes is greatly decreased compared to that of the peptides of SEQ ID NO: 3 and SEQ ID NO: 4 (FIG. 4B).

From the facts, it has been confirmed that although SEQ ID NO: 3 and SEQ ID NO: 4 have sequences similar to that of the peptide of SEQ ID NO: 2, the antimicrobial activity of the peptide of SEQ ID NO: 2 is remarkably increased compared to that of the peptides of SEQ ID NO: 3 and SEQ ID NO: 4 and the cytotoxicity of the peptide of SEQ ID NO: 2 is decreased compared to that of the peptides of SEQ ID NO: 3 and SEQ ID NO: 4, thus the effect of SEQ ID NO: 2 as an antimicrobial peptide is greatly superior to that of the peptides of SEQ ID NO: 3 and SEQ ID NO: 4, and not all peptides having similar sizes and similar sequences to those of the present disclosure have excellent antimicrobial activity.

Example 2: Evaluation of Antimicrobial Activity and Cytotoxicity of Antimicrobial Peptides Against Other Bacteria In order to evaluate whether the antimicrobial peptides of the present disclosure have antimicrobial activity against bacteria other than *Escherichia coli*, antimicrobial effects against *Escherichia coli, Staphylococcus aureus, Pseudomonas aeruginosa*, and *Candida albicans*, which were strains announced by the Ministry of Food and Drug Safety, were examined.

Specifically, *Escherichia coli, Staphylococcus aureus*, and *Pseudomonas aeruginosa* were cultured using LB medium, and *Candida albicans* was cultured using YM medium, and then the cultured bacteria were dispensed into a 96-well plate. Antimicrobial peptide samples at various concentrations were added into the respective wells, and incubation was performed at 37° C. for 24 hours. Absorbance was measured at 600 nm using a microplate reader, and the result was expressed as a percentage (%) with respect to that of the group not treated with the sample.

As a result, the $IC_{50}$ values showing the antimicrobial effect of the peptides of SEQ ID NO: 1 to SEQ ID NO: 8 against the four kinds of bacteria are as follows, and all SEQ ID NOs except SEQ ID NO: 3 and SEQ ID NO: 4 show strong antimicrobial effect against *Escherichia coli, Staphylococcus aureus, Pseudomonas aeruginosa*, and *Candida albicans* (Table 2).

TABLE 2

| | $IC_{50}$ (μM) | | | | | | | |
|---|---|---|---|---|---|---|---|---|
| | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| *Escherichia coli* | 21 | 14 | — | — | 12 | 9 | 11 | 10 |
| *Staphylococcus aureus* | 22 | 17 | — | — | 15 | 10 | 13 | 10 |
| *Pseudomonas aeruginosa* | 12 | 10 | — | — | 9 | 4 | 8 | 5 |
| *Candida albicans* | 19 | 13 | — | — | 11 | 6 | 10 | 8 |

In order to perform a disk diffusion test for the four kinds of bacteria, the following experiment was conducted.

After *Escherichia coli, Staphylococcus aureus, Pseudomonas aeruginosa*, and *Candida albicans* were cultured in the respective media, a certain amount of the cultured bacteria was spread on unhardened solid media, and then the media were hardened. On the surface of the hardened solid medium, 10 μL of antimicrobial peptide sample was placed, a dry 3M paper disk was put thereon, then incubation was performed at 37° C. for 16 hours, and the size of the zone of inhibition was observed.

As a result, it has been confirmed that when the peptide of SEQ ID NO: 6 was placed on the media spread with the respective kinds of bacteria for the disk diffusion method (Kirby-Bauer), transparent zones of inhibition with clear borders are observed on all the media spread with *Escherichia coli, Staphylococcus aureus, Pseudomonas aeruginosa*, and *Candida albicans* (FIG. 5).

Consequently, it has been confirmed that the antimicrobial peptides of SEQ ID NO: 5 to SEQ ID NO: 8 and derivatives thereof of the present disclosure exhibit remarkable antimicrobial activity not only against *Escherichia coli* but also against *Staphylococcus aureus, Pseudomonas aeruginosa*, and *Candida albicans.*

Example 3: Antimicrobial Effect of Antimicrobial Peptide by Destroying Cell Membrane of Microorganism In order to closely examine the effect of the antimicrobial peptide of the present disclosure on microorganisms, *Escherichia coli* was treated with the peptide of SEQ ID NO: 6 for 30 minutes, and then the antimicrobial effect was analyzed using a scanning electron microscope (SEM).

Specifically, for SEM analysis, *Escherichia coli* was cultured using LB medium, then a certain amount of cultured *Escherichia coli* was taken and treated with the peptide of SEQ ID NO: 6 for 30 minutes, washed with PBS 2 times, and then fixed with a primary fixative of 2% paraformaldehyde in PBS for 2 hours. After fixation, washing with PBS was performed 2 times, dehydration with 30%, 50%, 70%, 80%, 95%, and 100% ethanol was performed for 10 minutes in each step (the last treatment with 100% ethanol was repeated 3 times), and the pellets were lyophilized. After platinum coating using a coater, analysis by SEM was conducted.

As a result, when treated with the peptide of SEQ ID NO: 6, the entire cell membrane of *Escherichia coli* is destroyed to form large pores and elution of cell contents of the bacteria is observed (FIG. 6).

From the results described above, it has been confirmed that the antimicrobial peptides, derivatives thereof, or fragments thereof of the present disclosure have excellent antimicrobial activity and decreased cytotoxicity, and thus have a remarkable effect as antimicrobial peptides.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. An antimicrobial peptide consisting of any one of amino acid sequences of SEQ ID NO: 5 to SEQ ID NO: 8.

2. The antimicrobial peptide, according to claim 1, wherein the antimicrobial peptide inhibits growth of any one or more selected from the group consisting of *Escherichia coli, Staphylococcus aureus, Pseudomonas aeruginosa*, and *Candida albicans.*

3. A polynucleotide encoding the antimicrobial peptide according to claim 1.

4. The polynucleotide according to claim 3, wherein the antimicrobial peptide is encoded by any one of sequences of SEQ ID NO: 13 to SEQ ID NO: 16.

5. A carrier for external skin preparation comprising the antimicrobial peptide according to claim 1.

6. A cosmetic composition comprising the antimicrobial peptide according to claim 1.

7. A quasi-drug composition comprising the antimicrobial peptide according to claim 1.

8. A pharmaceutical composition for external skin preparation comprising the antimicrobial peptide according to claim 1.

* * * * *

SEQUENCE LISTING

```
<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<223> OTHER INFORMATION: antimicrobial peptide 1

<400> SEQUENCE: 1

Lys Lys Leu Phe Lys Lys Ile Leu Lys Tyr Leu Lys
1               5                   10


<210> SEQ ID NO 2
<211> LENGTH: 12
<212> TYPE: PRT
<213> ORGANISM: Artificial Sequence
<220> FEATURE:
<223> OTHER INFORMATION: antimicrobial peptide 2

<400> SEQUENCE: 2

Arg Arg Leu Phe Arg Arg Ile Leu Arg Tyr Leu Arg
1               5                   10


<210> SEQ ID NO 3
<211> LENGTH: 12
<212> TYPE: PRT
<213> ORGANISM: Artificial Sequence
<220> FEATURE:
<223> OTHER INFORMATION: antimicrobial peptide 3

<400> SEQUENCE: 3

Arg Phe Leu Phe Arg Leu Ile Leu Arg Tyr Leu Arg
1               5                   10


<210> SEQ ID NO 4
<211> LENGTH: 12
<212> TYPE: PRT
<213> ORGANISM: Artificial Sequence
<220> FEATURE:
<223> OTHER INFORMATION: antimicrobial peptide 4

<400> SEQUENCE: 4

Arg Arg Leu Phe Arg Leu Ile Leu Arg Tyr Leu Phe
1               5                   10


<210> SEQ ID NO 5
<211> LENGTH: 12
<212> TYPE: PRT
<213> ORGANISM: Artificial Sequence
<220> FEATURE:
<223> OTHER INFORMATION: antimicrobial peptide 5

<400> SEQUENCE: 5

Arg Lys Leu Phe Lys Arg Ile Leu Arg Tyr Leu Lys
1               5                   10


<210> SEQ ID NO 6
<211> LENGTH: 12
<212> TYPE: PRT
<213> ORGANISM: Artificial Sequence
<220> FEATURE:
<223> OTHER INFORMATION: antimicrobial peptide 6

<400> SEQUENCE: 6

Lys Arg Leu Phe Arg Lys Ile Leu Lys Tyr Leu Arg
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: antimicrobial peptide 7

<400> SEQUENCE: 7

Lys Arg Leu Phe Lys Arg Ile Leu Arg Tyr Leu Lys
1 5 10

<210> SEQ ID NO 8
<211> LENGTH: 12
<212> TYPE: PRT
<213> ORGANISM: Artificial Sequence
<220> FEATURE:
<223> OTHER INFORMATION: antimicrobial peptide 8

<400> SEQUENCE: 8

Arg Lys Leu Phe Arg Lys Ile Leu Lys Tyr Leu Arg
1 5 10

<210> SEQ ID NO 9
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 9
aaaaaactgt ttaaaaaaat tctgaaatat ctgaaa 36

<210> SEQ ID NO 10
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 10
cgccgcctgt ttcgccgcat tctgcgctat ctgcgc 36

<210> SEQ ID NO 11
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 11
cgctttctgt ttcgcctgat tctgcgctat ctgcgc 36

<210> SEQ ID NO 12
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 12
cgccgcctgt ttcgcctgat tctgcgctat ctgttt 36

<210> SEQ ID NO 13
<211> LENGTH: 36
<212> TYPE: DNA

-continued

```
<213> ORGANISM: Artificial Sequence
<220> FEATURE:
<223> OTHER INFORMATION: polynucleotide encoding antimicrobial peptide

<400> SEQUENCE: 13

cgcaaactgt ttaaacgcat tctgcgctat ctgaaa                              36


<210> SEQ ID NO 14
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 14

aaacgcctgt ttcgcaaaat tctgaaatat ctgcgc                              36


<210> SEQ ID NO 15
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 15

aaacgcctgt ttaaacgcat tctgcgctat ctgaaa                              36


<210> SEQ ID NO 16
<211> LENGTH: 36
<212> TYPE: DNA
<213> ORGANISM: Artificial Sequence
<220> FEATURE:
<223> OTHER INFORMATION: polynucleotide encoding antimicrobial peptide

<400> SEQUENCE: 16

cgcaaactgt ttcgcaaaat tctgaaatat ctgcgc                              36
```